United States Patent
Tanaka

(10) Patent No.: US 9,200,715 B2
(45) Date of Patent: Dec. 1, 2015

(54) PASSAGE-SWITCHING VALVE

(71) Applicant: SHIMADZU CORPORATION, Kyoto-shi, Kyoto (JP)

(72) Inventor: Shinji Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 68 days.

(21) Appl. No.: 14/357,292

(22) PCT Filed: Oct. 11, 2012

(86) PCT No.: PCT/JP2012/076274
§ 371 (c)(1),
(2) Date: May 9, 2014

(87) PCT Pub. No.: WO2013/069401
PCT Pub. Date: May 16, 2013

(65) Prior Publication Data
US 2014/0360605 A1 Dec. 11, 2014

(30) Foreign Application Priority Data

Nov. 11, 2011 (JP) ................. 2011-247387

(51) Int. Cl.
F16K 11/074 (2006.01)
F16K 11/085 (2006.01)
F16K 25/00 (2006.01)
G01N 30/22 (2006.01)
G01N 30/20 (2006.01)

(52) U.S. Cl.
CPC ......... F16K 11/0853 (2013.01); F16K 11/0743 (2013.01); F16K 25/00 (2013.01); G01N 30/22 (2013.01); G01N 2030/202 (2013.01); Y10T 137/86549 (2015.04)

(58) Field of Classification Search
CPC ............................ F16K 11/0743; F16K 25/00
USPC ..................................... 137/625.46
See application file for complete search history.

(56) References Cited

U.S. PATENT DOCUMENTS 3,780,758 A * 12/1973 DeVries .................... F16K 3/08
                                                137/454.6
4,632,148 A * 12/1986 Stark, Sr. ............. F16K 11/0743
                                                137/624.18
7,131,459 B2 * 11/2006 Beswick .............. A61C 1/0061
                                                137/625.11

(Continued)

FOREIGN PATENT DOCUMENTS

WO    2009/003519        1/2009
WO    2011/001941 A1     1/2011

OTHER PUBLICATIONS

Japanese Office Action dated Dec. 16, 2014 in Japanese Patent Application No. 2013-542898.
Chinese Office Action issued Dec. 3, 2014 in Chinese Patent Application No. 201280054883.3.

*Primary Examiner* — John Fox
(74) *Attorney, Agent, or Firm* — Sughrue Mion, PLLC

(57) ABSTRACT

Provided is a rotary passage-switching valve having a rotor with an extended service life. The passage-switching valve according to the present invention has a stator and a rotor which is rotatable while sliding relative to the stator. The stator has a plurality of ports whose ends are open on a sliding surface on which the rotor is made to rotate and slide. The rotor has a passage groove for connecting two or more of the ports. At an edge of the passage groove, the rotor is in contact with the sliding surface of the stator at a contact angle $\alpha$ greater than 120°.

7 Claims, 4 Drawing Sheets

(56) References Cited

U.S. PATENT DOCUMENTS 8,016,264 B2 * 9/2011 Takemasa .............. A61M 16/10 128/205.24
8,168,135 B2 * 5/2012 Hanafusa ............... B01L 3/5025 422/417
8,534,319 B2 * 9/2013 Bergeron .......... B01L 3/502738 137/151

* cited by examiner

THE INCREASED CONTACT ANGLE CAUSES DISPERSION OF INWARD-DEFORMING STRESS, AND IMPEDES DEFORMATION.

PASSAGE-SWITCHING VALVE

CROSS REFERENCE TO RELATED APPLICATIONS

This application is a National Stage of International Application No. PCT/JP2012/076274 filed Oct. 11, 2012, claiming priority based on Japanese Patent Application No. 2011-247387 filed Nov. 11, 2011, the contents of all of which are incorporated herein by reference in their entirety.

TECHNICAL FIELD

The present invention relates to a rotary passage-switching valve used in a liquid chromatograph or other devices having a switching passage.

BACKGROUND ART

Liquid chromatographs have a passage-switching valve for changing the passage according to the purpose, such as selecting a sample solution to be injected into a mobile phase or introducing a cleaning liquid for washing a column. A typical example of the channel-switching valve used in a liquid chromatograph is a rotary valve consisting of a stator having a plurality of ports (openings) individually connected to different passages and a rotor having a passage groove, where the rotor, while being strongly pressed against the stator, can be rotated and slid so as to connect the openings in the stator (Patent Literature 1).

In such a rotary passage-switching valve, in order to prevent a leakage of liquid between the stator and the rotor, a hard material (e.g. a metallic or ceramic material) is used for the stator, while a material (e.g. resin) softer than the stator is used for the rotor to improve the degree of contact with the stator. Furthermore, a high level of contact pressure (e.g. 50 MPa or higher) is applied to the sliding surfaces of the two elements.

CITATION LIST

Patent Literature

Patent Literature 1: WO 2011/001941 A

SUMMARY OF INVENTION

Technical Problem

In the rotary passage-switching valve, the rotor is rotated and slid while being constantly pressed against the stator with a high level of contact pressure. As noted earlier, the rotor is made of a softer material than the stator. Therefore, due to the high contact pressure applied to the sliding surfaces of the two elements and the friction with the stator during the rotation, a complex combination of compression and shear stresses acts on the microstructure of the rotor in the vicinity of the sliding surface, gradually causing a plastic deformation (creep). Due to this creep, the passage groove in the rotor becomes narrower, which may possibly result in the blocking of the passage in the passage-switching valve.

The rotor of the passage-switching valve is a replaceable part, and an unusably worn-out rotor can be replaced. However, frequently replacing the rotor requires more time and labor of the users and a higher operation cost. Furthermore, in the case of a continuous analysis using a liquid chromatograph with a plurality of liquid samples sequentially introduced into a mobile phase, the situation in which the analysis must be interrupted for the rotor replacement may occur.

The problem to be solved by the present invention is to extend the service life of the rotor in a rotary passage-switching valve.

SOLUTION TO PROBLEM

The present invention aimed at solving the aforementioned problem is a passage-switching valve having a stator and a rotor, the rotor being rotatable while sliding relative to the stator, the stator having a plurality of passages whose ends are open on a sliding surface on which the rotor is made to rotate and slide, and the rotor having a passage groove for connecting two or more of the plurality of passages, wherein:

the rotor, at an edge of the passage groove, is in contact with the sliding surface of the stator at a contact angle greater than 120°.

To prevent the narrowing of the passage groove due to the creep, a technique has conventionally been put into practice in which, at the edge of the passage groove, the rotor is provided with a portion sloping to the sliding surface between the rotor and the stator in such a manner that the groove widens toward the sliding surface (with the contact angle, or the edge angle of the rotor, set at 120°. However, in the case of a valve which is used an ultra-high performance liquid chromatograph (UH-PLC) and has a higher pressure resistance (e.g. up to 130 MPa) than a conventional valve (with a pressure resistance of up to 60 MPa) used in a high-performance liquid chromatograph (HPLC), the rotor is subjected to a complex stress of even higher levels of compression and shear. Under such conditions, even a rotor having the aforementioned structure with the contact angle of 120° cannot prevent the narrowing of the passage groove due to the creep, and the blocking of the passage in the passage-switching valve may occur with a small number of times of valve-switching operations (or uses). As a specific case, the blocking of the passage occurred before the number of times of the valve-switching operation exceeded 5000 in a continuous analysis performed under the condition that a non-polar solvent (e.g. chloroform or tetrahydrofuran (THF)) which can cause the swelling of a rotor material (e.g. PEEK (polyether ether ketone) or polyimide) and slightly decrease its strength was supplied at a low pressure of 30 MPa or less in a short cycle of one minute or less. The reason why the creep particularly occurs at such a low liquid-supply pressure is because lowering the liquid-supply pressure lessens the life-extending effects due to the liquid supply, such as the relaxation of the contact pressure between the stator and the rotor by the liquid-supply pressure or the fluid lubrication by the slight leakage of the supplied liquid.

The present inventor has manufactured a plurality of rotors with various contact angles and repeatedly conducted experiments. As a result, it has been revealed that making the contact angle larger than 120° improves the effect of suppressing the narrowing of the passage groove and increases the service life of the rotor in terms of the number of times of uses. For example, it has been found that a rotor with a contact angle of 150° can have a service life three to ten times longer than that of the conventional rotor with a contact angle of 120°.

ADVANTAGEOUS EFFECTS OF THE INVENTION

In the passage-switching valve according to the present invention, the rotor can be used a greater number of times than a rotor having a conventional structure. This reduces the time, labor and expenses for replacing the rotor. Furthermore, the situation in which an analyzing device needs to be halted in the middle of a continuous analysis is less likely to occur.

DESCRIPTION OF EMBODMENTS

One embodiment of the passage-switching valve according to the present invention is hereinafter described with reference to the attached drawings and in comparison with a conventional example of the passage-switching valve.

Figure 1:
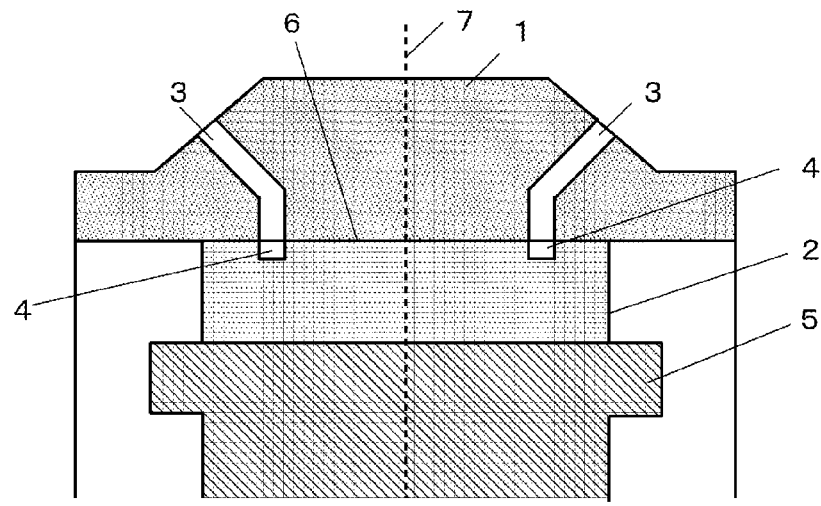
FIG. 1 is a vertical sectional view of a general structure of a rotary passage-switching valve.

FIG. 1 is a vertical sectional view showing the structure of a commonly used passage-switching valve. As shown, the rotary passage-switching valve includes a stator 1 having a plurality of ports 3 which can be connected to external passages, and a rotor 2 having channel grooves 4 for connecting the ports 3 with each other. The rotor 2 is pressed against the stator 1 via a shaft 5 supported with a spring or similar elastic member (not shown). By this pressure, a liquid-tight connection is maintained at the sliding surface 6 between the stator 1 and the rotor 2.

Figure 2A:
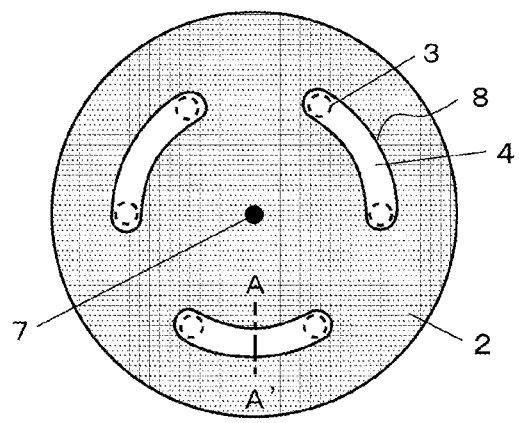
FIG. 2A is a top view of the structure of a rotor of a conventional example.
Figure 2B:
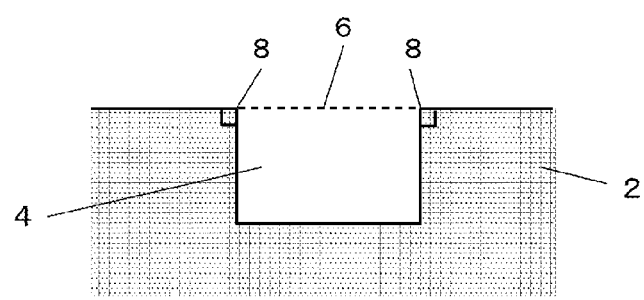
FIG. 2B is a sectional view at A-A' in FIG. 2A.

FIG. 2A is a top view of the rotor 2, and FIG. 2B is a sectional view at A-A' in FIG. 2A.

In FIG. 2A, the positions of the openings of the ports 3 are drawn in the broken lines to show the positional relationship between the ports 3 and the passage grooves 4. As shown in FIG. 2A, the rotor 2 has three arc-shaped passage grooves 4, each of which connects the openings of the two neighboring ports 3 among the six ports 3 of the stator 1. By connecting the two neighboring ports, each passage groove 4 forms an internal passage in the passage-switching valve. By revolving the rotor 2 around the rotation center 7, the connection of the two neighboring ports 3 is changed and the switching of the passage is achieved.

Figure 3A:
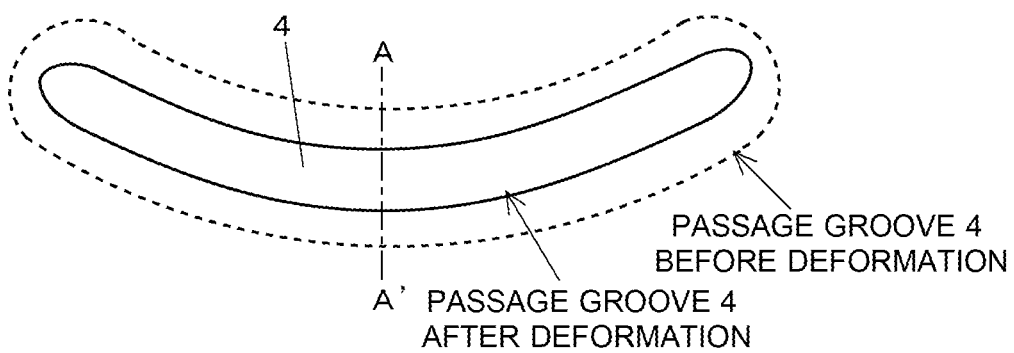
FIG. 3A is a top view for explaining a deformation of a channel passage.
Figure 3B:
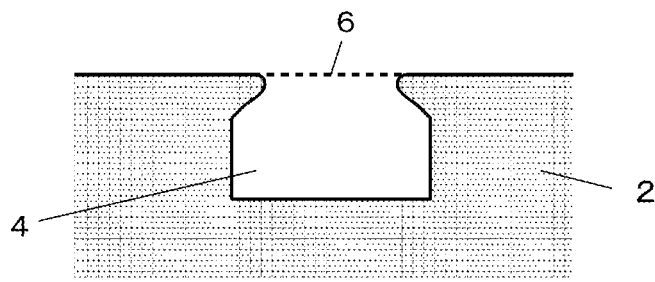
FIG. 3B is a sectional view at A-A' in FIG. 3A.

Normally, at the edge 8 of the passage groove 4, the rotor 2 is in perpendicular contact with the sliding surface 6 of the stator 1, as shown in FIG. 2B. Furthermore, the rotor 2 is normally made of a resin (e.g. polyether ether ketone or polyimide) softer than the metallic or ceramic stator 1, and this soft part is made to slide and rotate under high contact pressure. As a result, a creep occurs in the microstructure in the vicinity of the sliding surface 6 of the rotor 2. Due to this creep, the side surfaces of the passage groove 4 in the vicinity of the sliding surface 6 deform inwards and the groove becomes narrower, as shown in the top view of FIG. 3A and the vertical sectional view of FIG. 3B. If this deformation develops further, the passage groove 4 will be eventually closed, causing the blocking of the passage.

EMBODIMENTS

Figure 4:
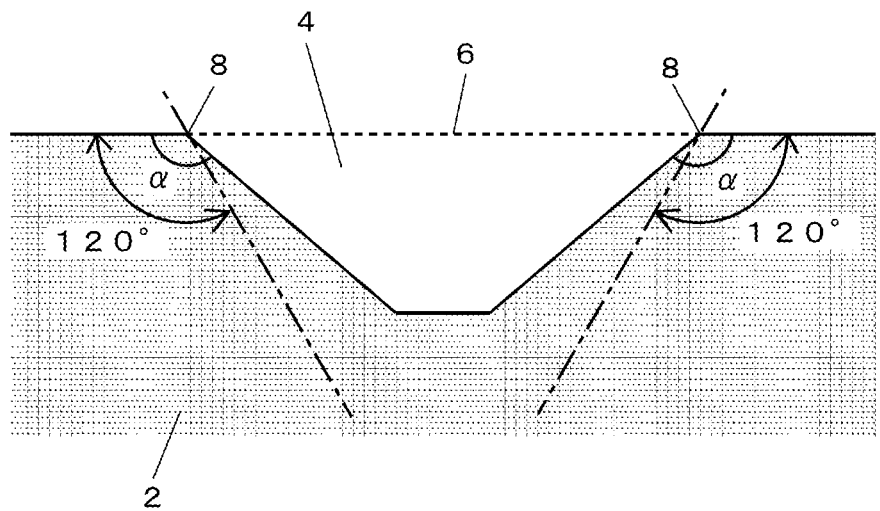
FIG. 4 is a passage-sectional view of a passage groove of a rotor showing one embodiment of the passage-switching valve according to the present invention.

FIG. 4 shows the passage-sectional shape of the passage groove 4 of the rotor 2 in the passage-switching valve of the present embodiment. As shown in this figure, in the present embodiment, the rotor 2 in contact with the sliding surface 6 of the stator 1 has a contact angle greater than 120° at the edge 8 of the passage groove 4.

Figure 5:
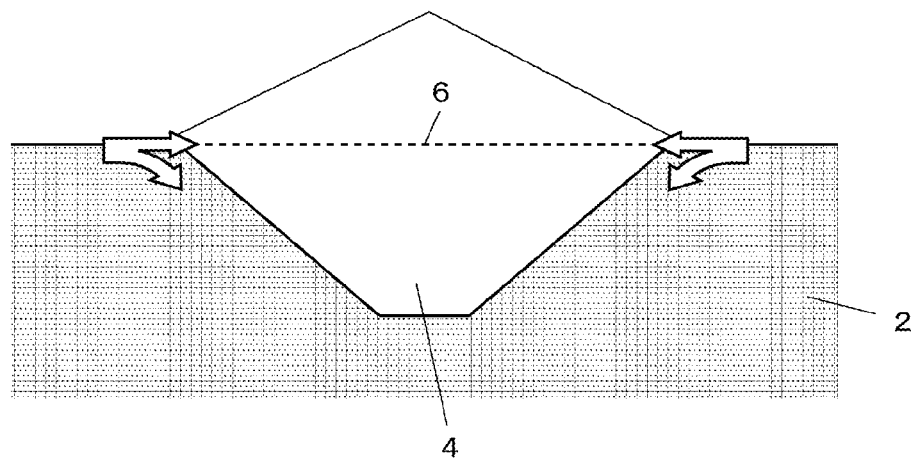
FIG. 5 is a passage-sectional view of the passage groove for explaining the rotor of the passage-switching valve of the present embodiment.

As shown in FIG. 5, when the contact angle α of the rotor 2 at the edge 8 is increased, the inward-deforming stress acting on the passage groove 4 does not concentrate on the edge 8 but becomes dispersed. Therefore, as compared to the groove shape of FIG. 2B in which the contact angle is 90° and the side surface of the passage groove 4 is at right angle to the sliding surface 6, the inward deformation is less likely to occur and the narrowing of the passage groove 4 is more effectively suppressed. Furthermore, since the passage groove 4 has a larger area on the sliding surface 6, the rotor 2 has a greater amount of allowance for the deformation due to the creep (i.e. an occurrence of creep is less likely to result in the blocking of the passage).

The idea of making the contact angle greater than 90° has also been conventionally put into practice. However, it has been thought that an excessive increase in the contact angle causes a change in the cross-sectional shape of the passage groove 4 due to the high contact pressure applied to the rotor 2, with a consequent decrease in the cross-sectional area of the passage. Therefore, the contact angle has conventionally been no greater than 120°. Questioning this hypothesis, the present inventor has manufactured a plurality of rotors with various contact angles and repeatedly conducted experiments. The results are shown in Table 1 below:

TABLE 1

| Contact Angle | Liquid-Supply Pressure | Analysis Cycle | Service Life |
| --- | --- | --- | --- |
| 120° | 5 MPa | 30 sec | 3,000-10,000 times |
| 150° | 5 MPa | 30 sec | 20,000-100,000 times |

It should be noted that the experimental results shown in Table 1 were obtained using the rotor 2 with the passage grooves 4 shaped as shown in FIG. 4.

As shown in Table 1, the experiment revealed that, with the contact angle of 120°, i.e. the largest conventional value, the rotor 2 became unusable after it was used approximately 3,000 to 10,000 times, whereas, the rotor 2 with the contact angle of 150° could be used approximately 20,000 up to 100,000 times. No particular decrease in the cross-sectional area occurred even in the case of the contact angle of 150°. Thus, it has been confirmed that making the contact angle greater than 120° dramatically extends the service life of the rotor 2 as compared to the conventional cases without causing any particular problem in the liquid supply. In Table 1, only the result obtained using the rotor with the contact angle of 150° belongs to the present embodiment. It should be noted that similar results were obtained for various contact angles ranging from 140° to 160°.

Figure 6A:
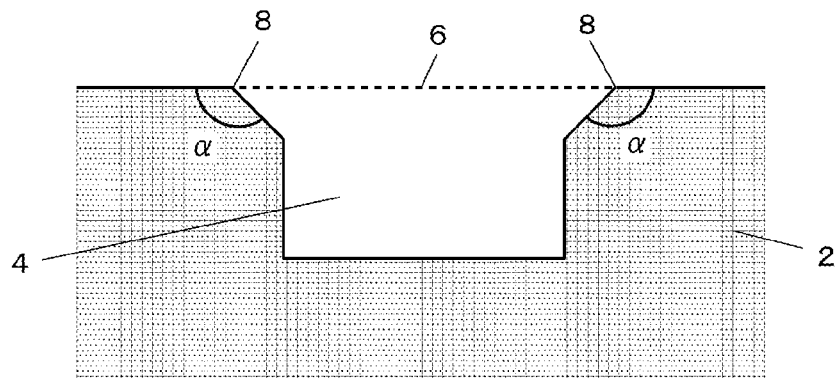
FIGS. 6A and 6B are passage-sectional views of the passage grooves of the rotors each of which shows a variation of the passage-switching valve of the present embodiment.
Figure 6B:
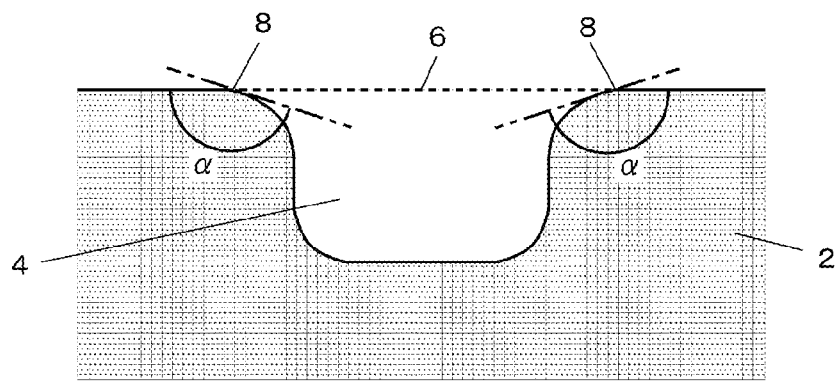

The creep of the rotor 2 mostly occurs in a region in the vicinity of the sliding surface 6 between the rotor 2 and the stator 1. Therefore, as shown in FIG. 6A, by increasing the inclination of the side surface of the passage groove 4 in the region in the vicinity of the sliding surface 6 while decreasing the inclination of the side surface of the passage groove 4 in the other region, it is possible to increase the passage-sectional area of the passage groove 4 while suppressing the narrowing of the passage groove 4 due to the creep. Accordingly, it is possible to make the contact angle α greater than the aforementioned 160°. The inclination of the side surface of the passage groove 4 may be gradually changed (FIG. 6B).

Figure 7:
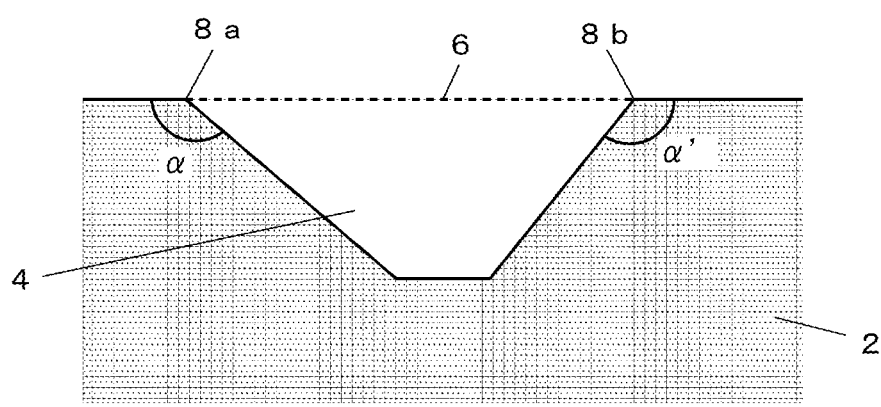
FIG. 7 is a passage-sectional view of the passage groove of the rotor showing another variation of the passage-switching valve of the present embodiment.

In FIG. 4, the contact angles of the rotor 2 at both edges of the passage groove 4 are the same. However, as shown in FIG. 7, the two contact angles may be different. For example, if the amount of creep occurring in the inner edge 8a of the rotor 2 is larger than that occurring in the outer edge 8b, it is preferable to adopt a design in which the contact angle α of the rotor 2 at the inner edge 8a is adequately large and the contact angle α' of the rotor 2 at the outer edge 8b is smaller than α.

Thus far, the passage-switching valve according to the present invention has been described by means of the embodiment. It is naturally possible to appropriately change or modify the embodiment within the spirit of the present invention.

REFERENCE SIGNS LIST

1 ... Stator
2 ... Rotor
3 ... Port
4 ... Passage Groove
5 ... Shaft
6 ... Sliding Surface
7 ... Rotation Center
8, 8a, 8b ... Edge

The invention claimed is:

1. A passage-switching valve having a stator and a rotor, the rotor being rotatable while sliding relative to the stator, the stator having a plurality of passages whose ends are open on a sliding surface on which the rotor is made to rotate and slide, and the rotor having a passage groove for connecting two or more of the plurality of passages, wherein:

the rotor, at an edge of the passage groove, is in contact with the sliding surface of the stator at a contact angle greater than 120°.

2. The passage-switching valve according to claim 1, wherein the contact angle is equal to or greater than 140° as well as equal to or less than 160°.

3. The passage-switching valve according to claim 1, wherein a side surface of the passage groove has areas with different inclinations in a depth direction.

4. The passage-switching valve according to claim 3, wherein a passage-sectional shape of the passage groove is asymmetrical in a width direction of the passage groove.

5. The passage-switching valve according to claim 2, wherein a side surface of the passage groove has areas with different inclinations in a depth direction.

6. The passage-switching valve according to claim 2, wherein a passage-sectional shape of the passage groove is asymmetrical in a width direction of the passage groove.

7. The passage-switching valve according to claim 1, wherein a passage-sectional shape of the passage groove is asymmetrical in a width direction of the passage groove.

* * * * *